United States Patent [19]

Bass et al.

[11] Patent Number: 4,767,777
[45] Date of Patent: Aug. 30, 1988

[54] TRIAZOLE ANTIFUNGAL AGENTS

[75] Inventors: Robert J. Bass, Birchington; Kelvin Cooper, Ramsgate; Kenneth Richardson, Canterbury, all of England

[73] Assignee: Pfizer Inc., New York, N.Y.

[21] Appl. No.: 797,737

[22] Filed: Nov. 14, 1985

[30] Foreign Application Priority Data

Nov. 27, 1984 [GB] United Kingdom ................. 8429932

[51] Int. Cl.$^4$ ...................... A61K 31/41; C07D 249/08
[52] U.S. Cl. ..................................... 514/383; 548/262
[58] Field of Search .......................... 548/262; 514/383

[56] References Cited

U.S. PATENT DOCUMENTS 4,618,616 10/1986 Richardson et al. ............... 514/340
4,664,696 5/1987 Schaub ..................... 71/92

FOREIGN PATENT DOCUMENTS 0180136 5/1986 European Pat. Off. ............ 548/341
2146987 5/1985 United Kingdom ................. 514/383

OTHER PUBLICATIONS

CA 105(15):133893b; Regel et al (1986).
CA 107(23):217636z; Ehrharst et al (1987).
CA 108(11):94558m; Blume et al.
CA 105(11):97481e; Cooper et al (1986).
CA 105(19):172468m; Regel et al (1986).
CA 104(23):207275e; Richardson et al (1985).

Primary Examiner—Glennon H. Hollrah
Assistant Examiner—D. L. Dinner
Attorney, Agent, or Firm—Peter C. Richardson; Albert E. Frost; James M. McManus

[57] ABSTRACT

A triazole of the formula

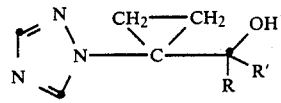

wherein R is phenyl substituted by difluoro, fluoro, dichloro or chloro and R' is phenyl substituted by chloro or fluoro are useful antifungal agents.

8 Claims, No Drawings

TRIAZOLE ANTIFUNGAL AGENTS

BACKGROUND OF THE INVENTION

This invention relates to novel triazole derivatives which have antifungal activity and are useful in the treatment of fungal infections in animals, including humans, and as agricultural fungicides.

British Patent Application No. 2,146,987A, published May 1, 1985, claims a series of antifungal agents of the formula

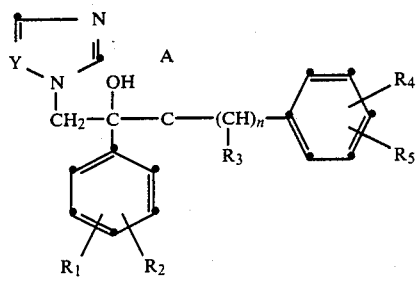

wherein $R_1$, $R_2$, $R_4$ and $R_5$ are aryl substituents; $R_3$ is hydrogen or alkyl, n is 0 or 1, Y is CH or N and A is a $C_2$-$C_7$ methylene bridge.

SUMMARY OF THE INVENTION

It has now been found that compounds of the structure

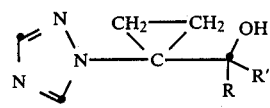

or an agriculturally acceptable acid addition salt thereof, wherein R is difluorophenyl, dichlorophenyl, fluorophenyl or chlorophenyl; and R' is fluorophenyl or chlorophenyl are useful in the treatment of plants or seeds having a fungal infection.

Preferred among these compounds are those wherein R is 2,4-difluorophenyl. Especially preferred within this class are compounds where R' is 4-chlorophenyl or 4-fluorophenyl.

The present invention also includes a method for treating a fungal infection in a plant or seed which comprises treating said plant or seed with an antifungal effective amount of a compound of formula (I), and a fungicidal composition for agricultural use comprising a compound of formula I together with an agriculturally acceptable diluent or carrier.

The invention further includes a pharmaceutical composition comprising an antifungal amount of a compound of formula (I) or a pharmaceutically acceptable acid addition salt together with a pharmaceutically acceptable diluent or carrier. It yet further includes a method of treating a fungal infection in an animal in need of such treatment which comprises administering to said animal an antifungal amount of a compound of formula (I) or pharmaceutically acceptable acid addition salt thereof.

The compounds of formula (I) can be prepared according to the following reaction scheme:

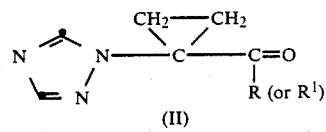

$R^1MgBr$, $R^1MgI$ or $R^1 Li$
(or $RMgBr$, $RMgI$ or $RLi$)

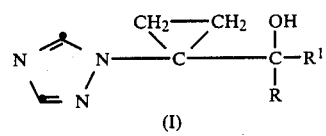

In a typical procedure, the ketone (II) and the Grignard or lithio derivative are stirred together at room temperature for a few hours in a suitable organic solvent, e.g. diethyl ether or tetrahydrofuran. If necessary, the mixture can be heated at up to the reflux temperature of the solution to accelerate the reaction. The product of the formula (I) can then be isolated and purified conventionally.

There are several methods for preparing the intermediates (II). These are illustrated schematically as follows, and equally "$R^1$" can be substituted for "R":

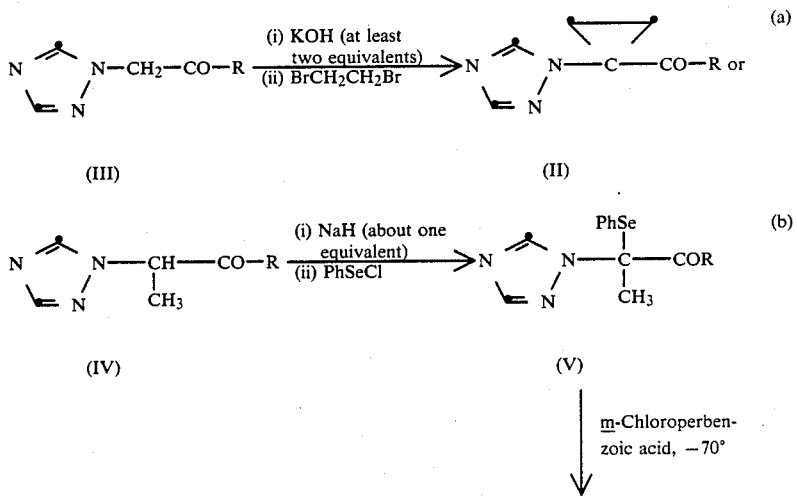

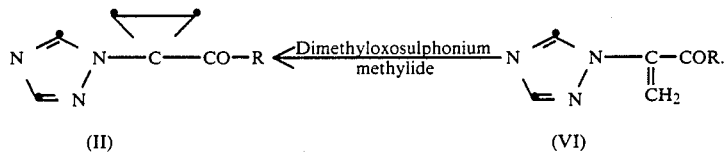

(II)    (VI)

In scheme (b), trimethylsulphoxonium iodide and aqueous sodium hydroxide/cetrimide can be used to generate dimethyloxosulphonium methylide in situ.

Scheme (a) is preferably carried out by adding "18-Crown-6-ether" (1,4,7,10,13,16-hexaoxacyclooctadecane) and potassium hydroxide (at least two equivalents to a solution of the ketone (III) in methylene chloride.

The Crown ether solubilizes the potassium hydroxide in methylene chloride, which is a non-polar solvent. After stirring for a few minutes, 1,2-di-bromoethane is added, and the reaction mixture is stirred at room temperature for up to about 24 hours. The ketone (II) can then be isolated and purified conventionally.

Scheme (a) can also be carried out in the absence of the Crown ether using dimethylsulphoxide as the solvent, but this is generally less satisfactory.

Scheme (b) is an alterantive to (a) but is a more complex route. Typical experimental details are given in Preparation 1.

The starting materials of the formula (III) are either known compounds or can be prepared by methods analogous to those of the prior art (see e.g. British Patent Specification Nos. 1512918 1533705 1533706 and European patent application publication Nos. 44605, 61051 and 69442).

The starting materials of the formula (IV) are described in our European patent application no. 122056. They can be prepared by simple route methods, typically as follows:

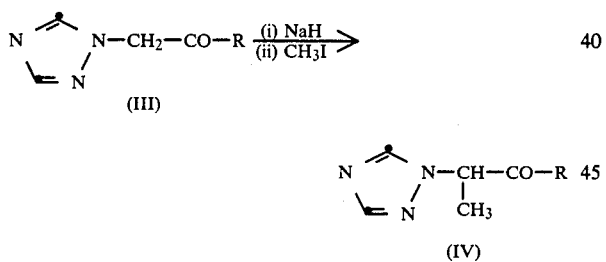

(III)

(IV)

The O-esters and O-ethers can be prepared conventionally, typically by reacting an alkali metal salt of compound (I) with the appropriate chloro- or bromocompound, e.g. an alkanoyl or benzoyl chloride, or alkyl, alkenyl, benzyl or phenyl chloride or bromide.

Pharmaceutically acceptable acid addition salts of the compounds of the formula (I) are those formed from strong acids which form non-toxic acid addition salts, such as hydrochloric, hydrobromic, sulphuric oxalic and methanesulphonic acids. Such salts are also useful for agricultural use.

The salts may be obtained by conventional procedures, e.g. by mixing solution containing approximately equimolar amounts of the free base and desired acid, and the required salt is collected by filtration, if insoluble, or by evaporation of the solvent.

The compounds of the formula (I) and their O-esters, O-ethers and salts are antifungal agents, useful in combating fungal infections in animals, including humans.

For example they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Asperigillus fumigatus,* Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compounds, in a suitable medium, at which growth of the particular micro-organism fails to occur. In practice, a series of agar plates, each having the test compound incorporated at a particular concentration is inoculated with a standard culture of, for example, *Candida albicans* and each plate is then incubated for 48 hours 37° C. The plates are then examined for the presence or absence of growth of the fungus and the appropriate m.i.c. value is noted. Other microorganisms used in such tests can include *Candida albicans, Aspergillus fumigatus,* Trichophyton spp; Microspoum spp; *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with, e.g., a strain of *Candida albicans* or *Aspergillus flavus.* Activity is based on the survival of a treated group of mice after the death of an untreated group of mice. The dose level at which the comopund provides 50% protection against the lethal effect of the infection ($PD_{50}$) is noted.

For human use, the antifungal compounds of the formula (I) and their salts, O-ethers and O-esters can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts, O-ethers and O-esters will be from 0.1 to 10 mg/kg (in divided doses) when administered by either the oral or parenteral route. Thus tablets or capsules of the compounds contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their O-ethers, O-esters and salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobulus carbonum, Pyricularia oryzae, Glomerella cingulata, Penicillin digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grians, or concentrates for dilution prior to use. Such compositions may contains such conventional carriers, diluents or adjuvants as are known and acceptable in agriculture and horticulture and they are manufactured in accordance with conventional procedures. The compositions typically contain from 0.01 to 95 wt %, preferably 0.01 to 1 wt %, of the active ingredient. The compositions may also incorporate other active ingredients, for example, compounds having herbicidal or insecticidal activity or a further fungicide. The compounds and compositions can be applied directly to the plant foliage, stems branches, seeds or roots or to the soil or other growing medium, and they may be used not only to eradicate disease, but also prophylactically to protect the plants or seeds from attack.

For field use, likely application rates of the active ingredient are from 5 to 500 g/10 ares.

The following Examples illustrate the invention. Temperatures are in ° C.:

EXAMPLE I 1,1-Bis-(4-fluorophenyl)-1-(1-[1H,1,2,4-triazol-1-yl]cyclopropyl)methanol

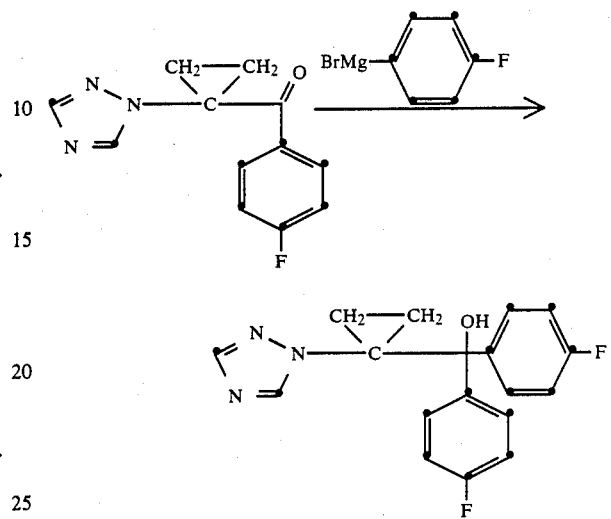

To a virgorously stirred suspension of magnesium turnings (0.15 g, 62.5 mMole) in dry ether, was added an ethereal solution of 4-bromofluorobenzene (1.05 g, 60 mMole) at such a rate that the mixture gently refluxed. Stirring was continued for another thirty minutes after the addition was complete. An ethereal solution of 1-(1H-1,24-triazol-1-yl)cyclopropyl 4-fluorophenyl ketone (1.15 g, 50 mMole) was then added dropwise and stirring was continued for three hours at room temperature (20° C.). The reaction mixture was then quenched with saturated aqueous ammonium chloride solution (30 ml) and the two phases were separated. The aqueous phase was washed with ether (50 ml) and the combiend organic phases were backwashed with saturated brine (20 ml) and then dried over anhydrous magnesium sulphate. Evaporation of the dried organic solution gave an oil which was purified by flash column chromatography on Merck "Kieselgel 60"(Trade Mark) 230–400 mesh silica (150 g), eluting with hexane/isopropyl alcohol (4:1). Collection and evaporation of the appropriate fractions gave a solid which was recrystallized from ethyl acetate to give the pure title compound, 0.516 g, m.p. 209°–10°(31.7% yield).

Analysis %: Calculated for $C_{18}H_{15}F_2N_3O$: C,66.05; H,4.62; N,12.84; Found: C,66.10; H,4.69; N,12.89.

N.m.r. and i.r. spectral data for the product were consistent with the stated structure.

EXAMPLES 2 TO 4

The following tertiary alcohols were prepared similarly to the method of Example 1 starting from a Grignard reagent of the formula $R^1MgBr$ and the ketone of the formula:

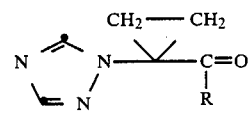

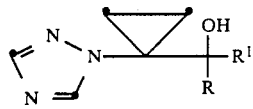

| Example No. | R | R¹ | m.p. (°C.) (and yield) | Analysis |
|---|---|---|---|---|
| 2 | 2,4-difluorophenyl | 4-chlorophenyl | 162-3° (45.5%) | Calculated for $C_{18}H_{14}ClF_2N_3O$: C, 59.76; H, 3.90; N, 11.61<br>Found: C, 59.79; H, 4.01; N, 11.66 |
| 3 | 2,4-difluorophenyl | 4-fluorophenyl | 200-1° (21%) | Calculated for $C_{18}H_{14}F_3N_3O$: C, 62.61; H, 4.09; N, 12.17<br>Found: C, 62.25; H, 4.15; N, 11.93 |
| 4 | 4-chlorophenyl | 4-chlorophenyl | 189-90° (43.5%) | Calculated for $C_{18}H_{15}Cl_2O$: C, 60.01; H, 4.20; N, 11.66<br>Found: C, 59.96; H, 4.20; N, 11.42 |

Similarly the ketone of Preparation 1(D) and 2 is reacted with 4-chloro- and 4-bromophenylmagnesium bromide to produce end products of the formula (I).

The following Preparations, in which all temperatures are in ° C., illustrate the preparation of certain starting materials.

Preparation 1

(A) 2',4'-Dichloro-2-(1H-1,2,4-triazol-1-yl)propiophenone hydrochloride

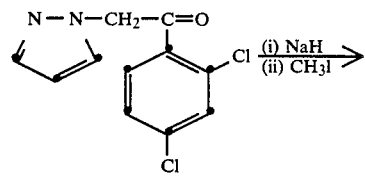

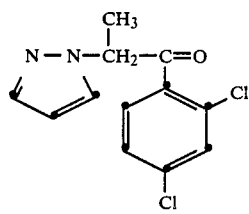

Alkylation of 2',4'-dichloro-2-(1H-1,2,4-triazol-1-yl)acetophenone (8.64 g) with methyl iodide (5.27 g) in the presence of sodium hydride (as a 50% dispersion in oil, total weight of dispersion 1.78 g) in tetrahydrofuran (150 ml) at 0° over 2 hours, yielded the title compound which was isolated as a hydrochloride salt, m.p. 125°–129°, 3.17 g (yield 34.8%).

Analysis %: Calculated for $C_{11}H_9Cl_2N_3O.HCl$. C,43.1; H,3.3; N,13.7; Found C,43.1; H,3.3; N,13.9.

N.m.r. and mass spectra data for the product were consistent with the stated structure.

(B) 2',4'-Dichloro-2-phenylseleneyl-2-(1H-1,2,4-triazol-1-yl)propiophenone

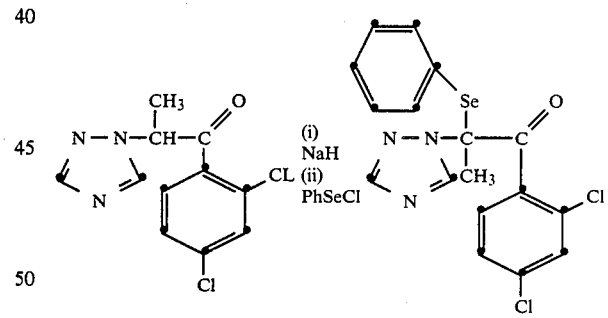

To a solution of 2', 4'-dichloro-2-(1H-1,2,4-triazol-1-yl)propiophenone (3 g, 11 mMole) in tetra-hydrofuran (60 ml) cooled to 5° was added sodium hydride as a 50% by weight dispersion in oil (0.68 g of said dispersion which contained 14 mMole of sodium hydride). Thirty minutes later phenylseleneyl chloride was added in four equal portions over five minutes (2.95 g, 15.4 mMole). Fifteen minutes later glacial acetic acid was added (1.5 ml) and the mixture was oured into water (100 ml). Excess solid sodium bicarbonate was added to basify the solution, which was then extracted with ethyl acetate (3×50 ml). The organic extracts were combined, washed with saturated saline solution (3×50 ml) and dried over anhydrous magnesium sulphate. Evaporation gave an impure oil, weight 5.4 g. Purification was carried out by flash column chromatography under slight pressure (2 p.s.i.) on a Merck Kiesselgel 60 (trade mark) 230-400 mesh silica-packed column, eluting with ether and 40°-60° petrol (1:1). The appropriate fractions after collection and evaporation gave a solid which was recrystallized from cyclohexane to give the pure title compound, 2.57 g, m.p. 84°-85° (47% yield).

Analysis %: Calculated for $C_{17}H_{13}Cl_2N_3OSe$: C,48.0; H,3.1; N,9.9; Found: #,48.0; H,3.2; N,10.2.

N.M.r., i.r. and mass spectral data for the product were consistent with the stated strucutre.

(C) 2',4'-Dichloro-2-(1H)-1,2,4-triazol-1-yl)-prop-2-enophenone

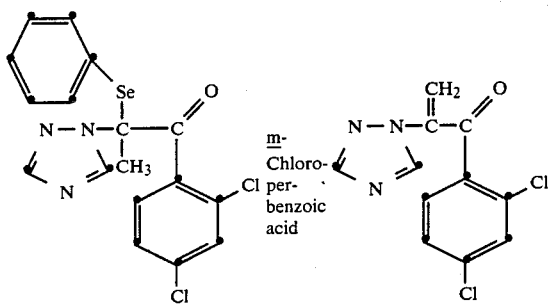

To a solution of the prorduct of Part (B) (0.42 g, 1.0 mMole) in methylene chloride (5 ml) at −72° was added metachloroperbenzoic acid (0.32 g, 1.5 mMole) in three equal portions over a twelve minute period. Two hours later the mixture, at −70°, was poured into an aqueous solution of saturated sodium bicarbonate and sodium sulphite (20 ml) with vigorous stirring. The organic layer was separated, washed with saturated sodium bicarbonate (3 ×5 ml) and water (3×5 ml), and dried over anhydrous sodium sulphate. Evaporation gave the title compound as an oil, 0.20 g, (74% yield). The compound was used directly in the next stage.

(D) 1-(1H-1,2,4-Triazol-1-yl)cyclopropyl 2,4-dichlorophenyl ketone

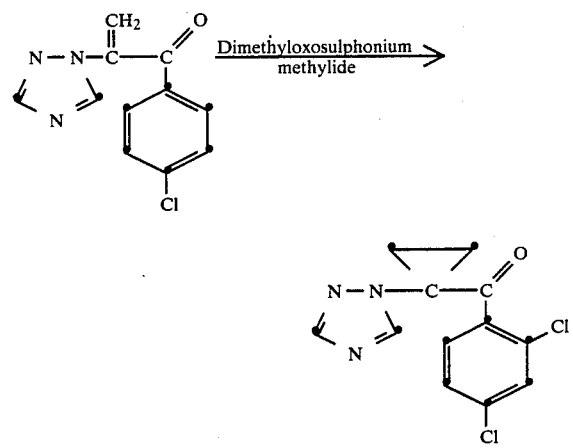

2',4'-Dichloro-2-(1H-1,2,4-triazol-1-yl)prop-2-enophenone (0.27 g, 1.0 mMole) was added dropwise in 1,1,1-trichloroethane (2 ml) to a refluxing mixture of trimethylsulphoxonium iodide (0.33 g, 1.5 mMole), cetrimide (0.03 g), 1,1,1-trichloroethane (5 ml) and aqueous 2N sodium hydroxide (3 ml) with vigorous stirring over 2 minutes. After refluxing for a further 15 minutes the organic phase, after cooling was separated. Evaporation gave a gum, weight 0.11 g.

Purification was carried out by flash column chromatography on Merck Kieselgel 60 (trade mark) 230-400 mesh silica, eluting with ether.

The appropriate fractions after collection and evaporation gave the pure title compound as a gum, 0.051 g, (18% yield).

N.m.r. and mass spectral data for product were consistent with the stated structure.

N.m.r (CDC$_3$). =1.85 (m,b 2H0, 2.1 (m, 2H), 7.1-7.25 (m,3H), 7.8 (s, 1H), 8.15 (s, 1H).

Analysis %: Calculated for $C_{12}H_9Cl_2N_3O$: C,51.1; H,3.2; N,.4.9; Found: C,50.8; H,3.0; N,15.0.

Preparation 2 [Alternative to Preparation 1 Parts (A) to (D)]

1-(1H-1,2,4-Triazol-1-yl)cyclopropyl 2,4-dichlorophenyl ketone

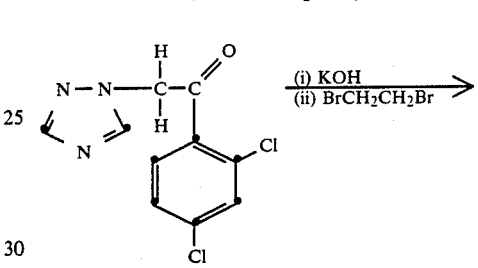

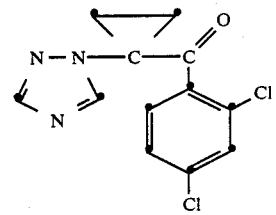

Potassium hydroxide (4.88 g, 88 mMole) was added to a solution of 2-(1H-1,2,4-triazol-1-yl)-2', 4'-dichloroacetophenone (see British patent application Publication No. 2078719A) (10.24 g, 40 mMole) in dimethylsulphoxide (100 ml). Thirty minutes later 1,2-bromoethane was added in one batch (8.28 g, 44 mMole) with stirring.

Stirring was continued for 20 hours.

The mixture was then poured into water (175 ml) and extracted with methylene chloride (3×50 ml). The organic extracts were combined and washed with water (3×50 ml).

The solution was dried over anhydrous magnesium sulphate and evaporated to a gum, weight 11.92 g. Purification was carried out by flash column chromatography under slight pressure (2 p.s.i.) on a Merck "Kieselgel 60" (trade mark) 230-400 mesh silica-packed column, eluting with ether.

The appropriate fractions after collection and evaporation gave a gum which solidified on standing to give the pure title compound, 2.51 g, m.p. 55°-56° (22.2% yield).

N.m.r. and mass spectral data for the product were consistent with the stated structure. The compound was confirmed spectroscopically to be identical to the product of Preparation 1(D).

Preparation 3

1-(1H-1,2,4-triazol-1-yl)cyclopropyl 4-fluorophenylketone

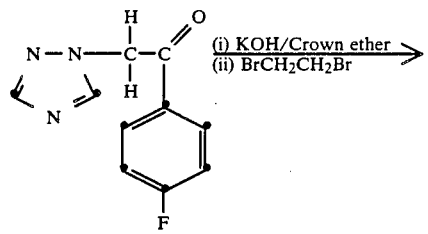

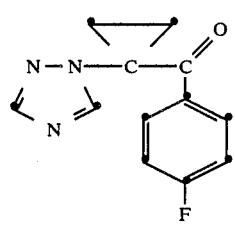

To a solution of 2-(1H-1,2,4-triazol-1-yl)-4'-fluoroacetophenone (10.24 g, 50 mMole) in methylene chloride (70 ml) was added 18-Crown-6 ether (1 g) trade mark for 1,4,7,10,13,16-hexaoxacyclooctadecane) and potassium hydroxide (6.1 g, 109 mMole) with stirring. Ten minutes later 1,2-dibromoethane was added (10.3 g, 55 mMole) in one batch. Stirring was continued for 18 hours. The mixture was poured into saturated saline solution (100 ml) and the organic phase was separated, washed with water (3×30 ml) and dried over anhydrous magnesium suphate. Evaporation gave an oil, weight 1.7 g. Purification was carried out by flash column chromatography under slight pressure (2 p.s.i.) on a Merck "Kieselgel 60" (trade mark) 230-400 mesh silicapacked column eluting with ether. The appropriate fractions after collection and evaporation gave a solid, the pure title compound, 2.9 g, m.p. 73°–75° (25% yield).

Analysis % Calculated for $C_{12}H_{10}FN_3O$: C,62.3; H,4.5; N,18.3; Found: C,62.3; H,4.4; N,18.2.

N.m.r., i.r. and mass spectral data for the product were consistent with the stated structure.

2-(1H-1,2,4-Triazol-1-yl)-4'-fluoroacetophenone was prepared by procedures analogous to those described in GB No. 20788719A.

Preparations 4 and 5

The following ketones were prepared similarly to the method of the preceding Preparation from the appropriate starting materials.

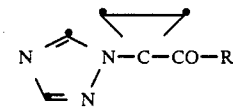

| Preparation No. | R | m.p. (°C.) and yield | Analysis % |
|---|---|---|---|
| 4 | 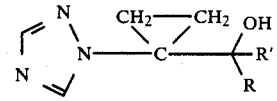 F, F | 89–90° (yield 23.3%) | Calculated for $C_{12}H_9F_2N_3O$: C,57.8; H,3.6; N,16.9; Found: C,57.9; H,3.6; N,16.6. |
| 5 | Cl | 89–90° (yield 25.4%) | Calculated for $C_{12}H_{10}ClN_3O$: C,58.2; H,4.0; N,17.0; Found: C,58.3; H,4.0; N,17.0. |

The prepration of the starting material 2-(1H1,2,4-triazol-1-yl)-2',4'-difluoroacetophenone is described in European patent application publication no. 69442. 2-(1H-1,2,4-Triazol-1-yl)-4'-chloroacetophenone was prepared similarly.

Using the method described in the text, the oral $PD_{50}$ values after 48 hours against mice infected with C. albicans are as follows:

| Compound | $PD_{50}$ (mg./kg.) |
|---|---|
| Product of Example 1 | <1 |
| Product of Example 2 | 0.47 |
| Product of Example 3 | 0.3 |
| Product of Example 4 | <1 |

We claim:
1. A compound of the formula:

or a pharmaceutically or agriculturally acceptable acid addition salt thereof, wherein R is selected from the group consisting of difluorophenyl, dichlorophenyl, fluorophenyl and chlorophenyl; and R' is selected from the group consisting of fluorophenyl and chlorophenyl.

2. A compound of claim 1, wherein R is 2,4- difluorophenyl.

3. The compound of claim 2, wherein R' is 4-chlorophenyl.

4. The compound of claim 2, wherein R' is 4-fluorophenyl.

5. A method of treating a fungal infection in a plant which comprises treating said plant with an antifungally effective amount of a compound or agriculturally acceptable acid addition salt according to claim 1.

6. A fungicidal composition for agricultural use, comprising onantifungal amount of a compound or agriculturally acceptable acid addition salt according to claim 1 and an agriculturally acceptable diluent or carrier.

7. A pharmaceutical composition comprising an antifungal amount of a compound or pharmaceutically acceptable acid addition salt according to claim 1 and a pharmaceutically acceptable diluent or carrier.

8. A method of treating a fungal infection in an animal in need of such treatment which comprises administering to said animal an antifungal amount of a compound or pharmaceutically acceptable acid addition salt according to claim 1.

* * * * *